(12) United States Patent
Hill et al.

(10) Patent No.: US 7,949,506 B1
(45) Date of Patent: May 24, 2011

(54) METHOD FOR DETERMINING AND COMPENSATING FOR A WEIGHT LOSS ENERGY GAP

(75) Inventors: James Hill, Englewood, CO (US); Holly Wyatt, Denver, CO (US)

(73) Assignee: Active Planet llc, Denver, CO (US)

( * ) Notice: Subject to any disclaimer, the term of this patent is extended or adjusted under 35 U.S.C. 154(b) by 47 days.

(21) Appl. No.: 11/296,069

(22) Filed: Dec. 6, 2005

(51) Int. Cl.
*G06G 7/58* (2006.01)
(52) U.S. Cl. .................. 703/11; 702/19; 703/2; 700/28; 706/11
(58) Field of Classification Search .................. None
See application file for complete search history.

(56) References Cited

U.S. PATENT DOCUMENTS

| | | | |
|---|---|---|---|
| 2003/0226695 A1* | 12/2003 | Mault | 177/25.16 |
| 2005/0240434 A1* | 10/2005 | Wooten et al. | 705/2 |

* cited by examiner

*Primary Examiner* — Carolyn L. Smith
(74) *Attorney, Agent, or Firm* — Baker Hostetler

(57) ABSTRACT

The present invention provides a weight loss maintenance system. The invention incorporates supplements (dietary, pharmaceutical or neutraceutical) that aid in maintaining weight loss as well as physical activity. The invention further provides a personal plan that can include instruction, ideas and support based on user input, indicated preferences and various calculations. This invention calculates an Energy Gap™ that is produced by a specific amount of weight loss in an individual and fills this quantitative energy gap with activity and/or products which reduce hunger and/or increase metabolic rate.

7 Claims, 6 Drawing Sheets

Lets find your Energy Gap
Instructions: fill in the answers below and click Calculate My Energy Gap.

Height (inches): [68] — 200

Current Weight (lbs.): [205] — 220

Gender: [Female] — 230

Age: [40] — 240

Weight Loss: [30] — 250

How much physical activity (in steps or minutes) did you average BEFORE you lost any weight, or currently if you have not lost any weight?

[Minimal: Less than 3,000 steps/day or 30 minutes of activity ▼] — 260

In the 3 months BEFORE you started to lose your weight, which option best describes your weight trend (stability)

[I gained between 3 and 5 lbs in those 3 months ▼] — 270

FIG. 3

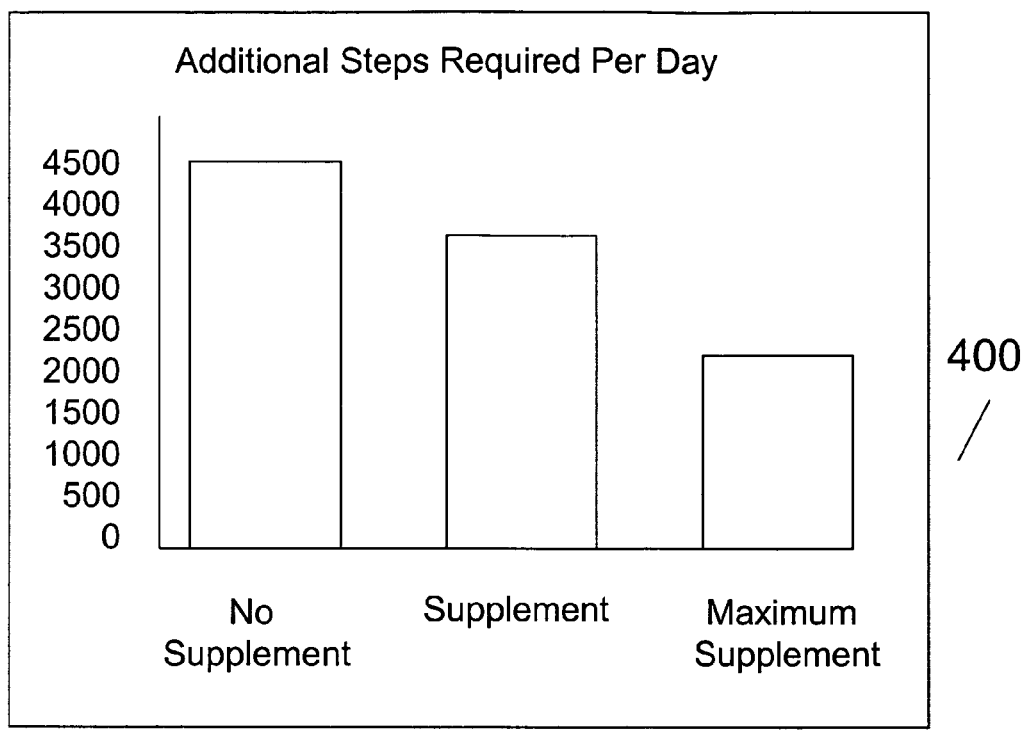
FIG. 5
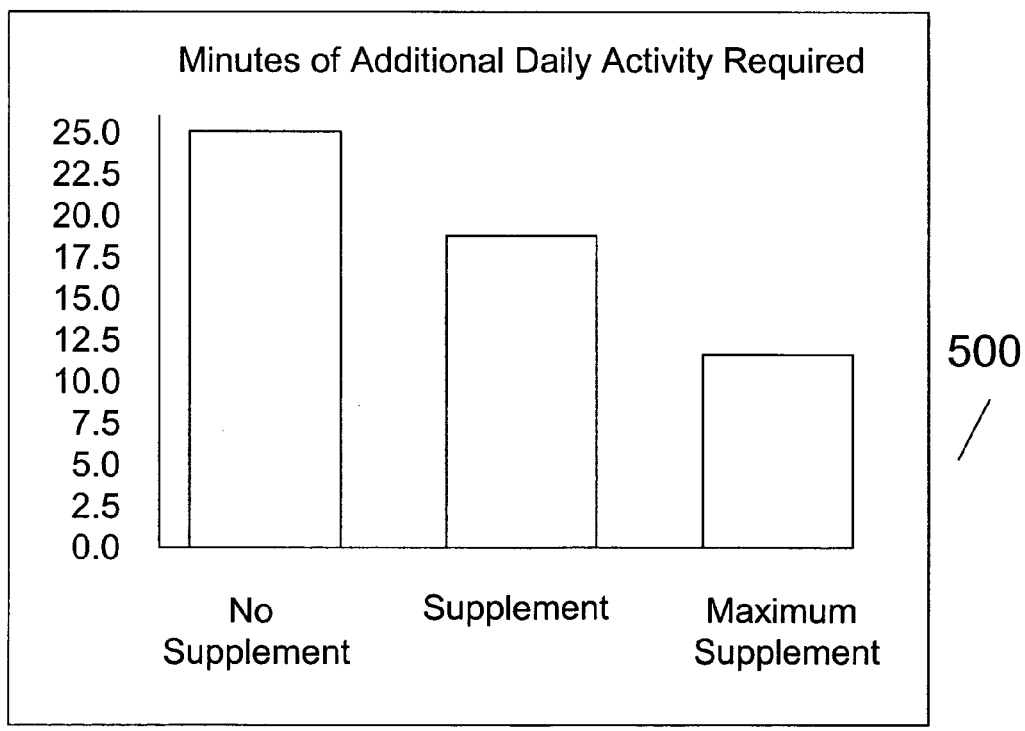

METHOD FOR DETERMINING AND COMPENSATING FOR A WEIGHT LOSS ENERGY GAP

BACKGROUND OF THE INVENTION

1. Field of the Invention

The invention relates generally to weight loss maintenance, obesity treatment, and more particularly to methods and apparatus for developing specific and customized weight maintenance plans.

2. Description of Related Art

The weight loss industry in the United States has become a multi-billion dollar industry. Most weight management programs are successful at producing weight loss but unsuccessful at keeping the weight off. This is because most provide specific advice for weight loss but no specific advice for maintenance of weight loss. Instead, they rely primarily on chronic caloric restriction, which is effective for weight loss but not for weight loss maintenance. Any advice given about physical activity is very general, such as exercise more. There are not currently any methods or apparatus that allow development of specific goals for weight loss maintenance. For example in a weight management program such as Weight Watchers™ a participant who is trying to lose weight or maintain a certain weight is allowed a certain number of food points per day/week. If that participant also exercises the allowable number of food points is increased. However, the amount of exercise or activity is not quantified and the general weight management plan or the food points that are recommended do not take into consideration dietary supplements, additional weight loss products, or other innovative weight maintenance strategies that may impact the long-term intake requirements. Most weight management programs emphasize continuous long-term caloric restriction with little or minimal adjustments for both the amount of the participant's initial weight loss or for optimizing their long-term weight loss maintenance plan.

Weight loss and weight loss maintenance are different physiological and behavioral processes, and many of the strategies that work best for weight loss (primarily caloric restriction) may not be optimal or as effective for weight loss maintenance or simply weight maintenance. For example, the process of successful weight loss requires strategies that are typically carried out for relatively short periods of time (less then 6 months) and require a negative energy balance (eating less calories then one is expending), while the process of successful weight loss maintenance requires strategies that can be carried out for very long periods of time (many years or a lifetime) and require the participant to remain in energy balance (eating the same amount of calories as one expends over time). Caloric restriction (dieting) is a common strategy that works well for short periods of time and produces a large negative energy balance and therefore produces successful weight loss. Many people have succeeded at using this strategy to lose weight and most weight management programs focus on this strategy. Caloric restriction however is a strategy that is very hard for most people to sustain for long periods of time. Caloric restriction has proven to be a non-effective strategy for long-term weight loss maintenance.

While strictly increasing physical activity is not as effective as caloric restriction, many experts recognize that increasing physical activity is a better strategy for long-term weight loss maintenance. However, there is currently no way to develop specific and individualized goals for how much physical activity is required for weight loss maintenance. Because weight loss and weight maintenance are different processes a different strategy, plan or emphasis may need to be used to optimize success for both initial weight loss and for maintaining the reduction in body weight long-term. The major barrier to successful maintenance of weight loss is the changes in human physiology and energy metabolism that occur as one loses body weight. These changes leave individuals who have lost weight with lower caloric needs than before weight loss and necessitate permanent changes in caloric intake and/or physical activity in order to meet the new, lower caloric requirements. For example, when a person goes on a diet and restricts their calorie intake, they lose body weight and as a result their metabolism (energy expenditure, the calories they burn) also decreases. This is why people generally lose weight faster at the beginning of a dieting period than near the end. At the end of the diet period their metabolism or energy expenditure has decreased so that the same reduction in food calories or the same diet plan does not produce as large of negative energy balance and thus weight loss slows or stops while they continue the caloric restriction. When they eventual stop restricting calories, the decrease in energy metabolism results in their body burning fewer calories and in an increased likelihood of a positive energy balance (energy intake greater then energy expenditure) and thus weight regain occurs. This is also why many crash/fad diets are so popular—because by the time the metabolism slows by a significant amount, they have lost some weight quickly which represents a short term successful weight loss. However, this is also why most fad/crash diets fail. Because not only do most people begin increasing the daily caloric intake again, but they do so while their metabolism is operating at a reduced level from the weight reduction. Thus, the result is that not only do people gain back the original weight that was lost, but they often gain additional weight as well. The caloric restriction strategy for weight loss works well for short-term weight loss but sets the person up to regain weight once they can no longer adhere to the diet and restrict food calories. Thus a vicious circle of weight loss followed by weight regain is formed.

For these reasons, a weight loss maintenance program is required in addition to a weight loss program for comprehensive and sustainable weight management. Because of the reasons discussed, an optimal and successful weight maintenance program will differ from a weight loss program. When a person loses weight their (smaller mass) body requires less energy (or food calories) each day, but their appetite (drive to eat) does not automatically decrease just because of the weight loss. Thus an energy gap is created between the food energy a body desires and the smaller amount of food energy it needs to maintain the new reduced body size. This energy gap causes the body to regain the weight that was lost unless the person compensates with new strategies that take into account and minimize the gap.

Accordingly it would be advantageous to provide an individualized weight loss maintenance program that takes into account and compensates for the energy gap that is created following a weight loss. It would also be advantageous to provide such a program that considers one or more variables such as pre-weight loss body weight, body fat percentage, types and duration of exercise, types of food generally eaten, supplements, and post-weight loss body fat percentage, exercise, supplements, and types of food eaten.

BRIEF SUMMARY OF THE INVENTION

These and other advantages are attained by the present invention which in one aspect provides systems and methods for maintaining weight loss.

Implementations of the invention may provide one or more of the following features. A method and apparatus for calculating an energy gap caused by caloric restriction and weight reduction and providing a specific, customized weight maintenance plan which may include instruction, ideas and support, based on user input, indicated preferences, and the energy gap calculations.

An aspect of the invention provides a method for developing a weight maintenance program. The method includes receiving statistics about a person, wherein at least one of the statistics relates to the person prior to starting a weight loss and at least another of the statistics relates to the person at the completion of the weight loss. The method also includes determining a pre-weight loss energy requirement based at least in part on the at least one pre-weight loss statistic and determining a post-weight loss energy requirement based at least in part on the at least one completion-weight loss statistic.

Another aspect of the invention provides an apparatus for determining a weight maintenance program. The apparatus includes an interface for accepting statistics. At least one of the statistics relates to a person prior to losing weight and starting a diet and at least another of the statistics relates to the person after weight loss at the completion of the diet. The apparatus also includes a processor in electrical communication with the interface and configured to determine a pre-diet pre-weight loss energy requirement based at least in part on the at least one pre-weight loss statistic and to determine a post-weight loss energy requirement based at least in part on the at least one completion-diet statistic. The processor is also configured to determine a program for compensating for a difference between the pre-diet pre-weight loss and post-diet post-weight loss energy requirement. The apparatus also includes a display in electrical communication with the processor and configured to display the program determined by the processor.

Another aspect of the invention provides an apparatus for determining a weight loss maintenance program. The apparatus includes an input module for inputting gender, height, pre-weight loss weight, age, weight loss, pre-weight loss physical activity and pre-weight loss weight stability. The apparatus also include a processing module, in electrical communication with the input module. The processing module is configured for generating an appropriately lower Resting Metabolic Rate (RMR) due to weight loss, generating physical activity energy values for the same physical activity performed pre-weight loss and post-weight loss, determining a difference between the physical activity energy values, generating an adjustment value based on the weight stability, summing the lower RMR, the difference between the physical activity energies and the adjustment value, and determining a combination of exercise, supplements and food necessary to maintain the reduced body weight. The apparatus also includes a display in electrical communication with the processing module. The display is configured to display the combination of exercise, supplements and food.

Yet another aspect of the invention provides a method of developing a program for maintaining a particular body weight which includes receiving a current body weight of a person desiring to maintain a particular body weight. The method further includes calculating a Resting Metabolic Rate (RMR) of the person based at least in part on the received current body weight and determining a combination of exercise, supplements and food necessary to maintain the particular body weight, based at least in part on the RMR.

The invention will next be described in connection with certain illustrated embodiments and practices. However, it will be clear to those skilled in the art that various modifications, additions and subtractions can be made without departing from the spirit or scope of the claims.

BRIEF DESCRIPTION OF THE SEVERAL VIEWS OF THE DRAWINGS

The invention is herein described, by way of example only, with reference to the accompanying drawings, wherein:

FIG. 3 illustrates sample input and output in accordance with the invention of FIG. 1.

FIG. 5 illustrates a sample energy gap plan with graphical and written representation.

DETAILED DESCRIPTION OF THE INVENTION

Figure 1:
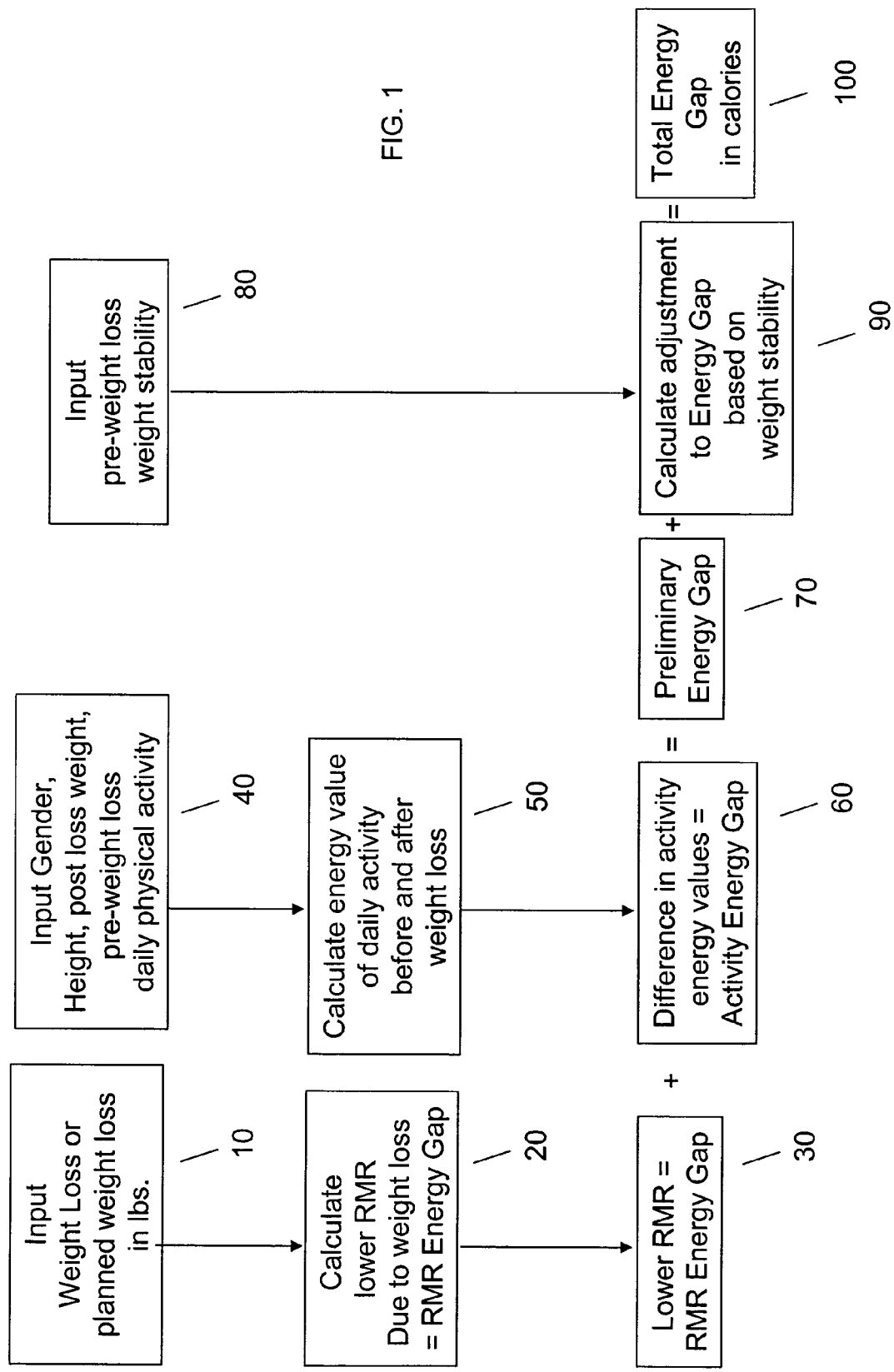
FIG. 1 illustrates a flow diagram in accordance with an aspect of the invention.

Referring to the drawings in detail wherein like reference numerals identify like elements throughout the various figures, there is illustrated in FIGS. 1-6 systems and methods according to the present invention. The principles and operations of the present invention may be better understood with reference to the drawings and the accompanying description.

The invention provides systems and methods for determining a weight-loss maintenance program. The invention may be embodied in software, hardware or as a method of doing business and may reside on a stand-alone computer, a wireless device, on a network computer, a network server or any other location capable of receiving input and providing output. The invention may be accessed directly or remotely depending upon the embodiment. For ease of explanation the following description will be limited to use of the invention via the Internet, however, this is in no way meant to limit the scope of the invention to the Internet.

When a person diets by eating fewer calories per day that individual begins to lose weight, but their energy metabolism also begins to decrease as they lose body weight. As such, after a while that person needs to eat even fewer calories to continue to lose additional weight or must continue to restrict calories to maintain the current reduced body weight. Thus, there is a difference between the energy a person is consuming to maintain a certain body weight before energy restriction and weight loss and the amount of energy required by the body to be consumed to maintain a reduced body weight following a weight loss. This difference in energy (calories) will be referred to herein as the Energy Gap™.

An aspect of the invention, illustrated in FIG. 1, provides a method for determining the Energy Gap™ for an individual based on various data about that individual. Those skilled in the art will recognize that the Energy Gap™ could be based on actual information or desired information (i.e. for planning future weight loss). Additionally, it could be used for a specific person or it could be generalized for more people.

The determination of the Energy Gap™ is preferably determined in calories although those skilled in the art will recognize that other units of measure could be employed without departing from the scope of the invention. As seen from FIG. 1, the invention accepts input 10 in the form of amount of weight lost or planned weight loss (for a person who is looking for a program to maintain their current weight without weight-loss, they can enter a 0 for the planned weight loss value and/or the same number for both current and pre-weight-loss weight). It also accepts gender, height, current weight and pre-weight loss weight, daily physical activity and pre-weight loss stability (i.e. the status of the person's weight for a specified period prior to the start of the diet). The input could be in the form of text entered via a keyboard, a selection from a menu (using a mouse or a keypad), DTMF tones from a phone or voice which is converted into usable data etc. While this is the preferred input, those skilled will recognize that there are many variables that can be entered for determining the Energy Gap™. For example, less than all of the above information could be employed, additional information could be employed (such as body fat percentage before and after the diet, various body measurements such as waist, chest, etc.), or different combinations of the above information.

In a preferred embodiment, the invention uses some of the information provided, such as the weight loss amount 10, to determine a post weight loss (lower) Resting Metabolic Rate (RMR) 20. This lower RMR shall be referred to as the RMR Energy Gap™ 30. The invention also uses some or all of the information 40, such as gender, height, pre-diet weight and pre-diet daily physical activity, to determine energy values of daily activity before and after weight loss 50. The difference between these two values will be referred to as the Activity Energy Gap™ 60. These two Energy Gap™ values may be summed to determine a preliminary total Energy Gap™ 70. However, this step may be skipped and performed simultaneously with the final calculation. The invention also employs the pre-weight loss weight stability 80 to generate an adjustment value 90 for the Energy Gap™. The invention then determines a Total Energy Gap™ 100 by summing the preliminary Total Energy Gap™ 70 with the adjustment value 90 or by summing the RMR Energy Gap™ 30, the Activity Energy Gap™ 60 and the adjustment value 90. While each of these numbers has been illustrated as calculations, it is within the scope of the invention that these may simply be looked up in a table based on the input information. Further, rather than providing discrete numbers the system could provide ranges of values as the resulting Energy Gaps™

This Total Energy Gap™ 100 may be provided to the end user. It can be displayed on a display unit in the form of a number or a graph, or it can be converted to voice and provided to the user in that way.

Figure 2:
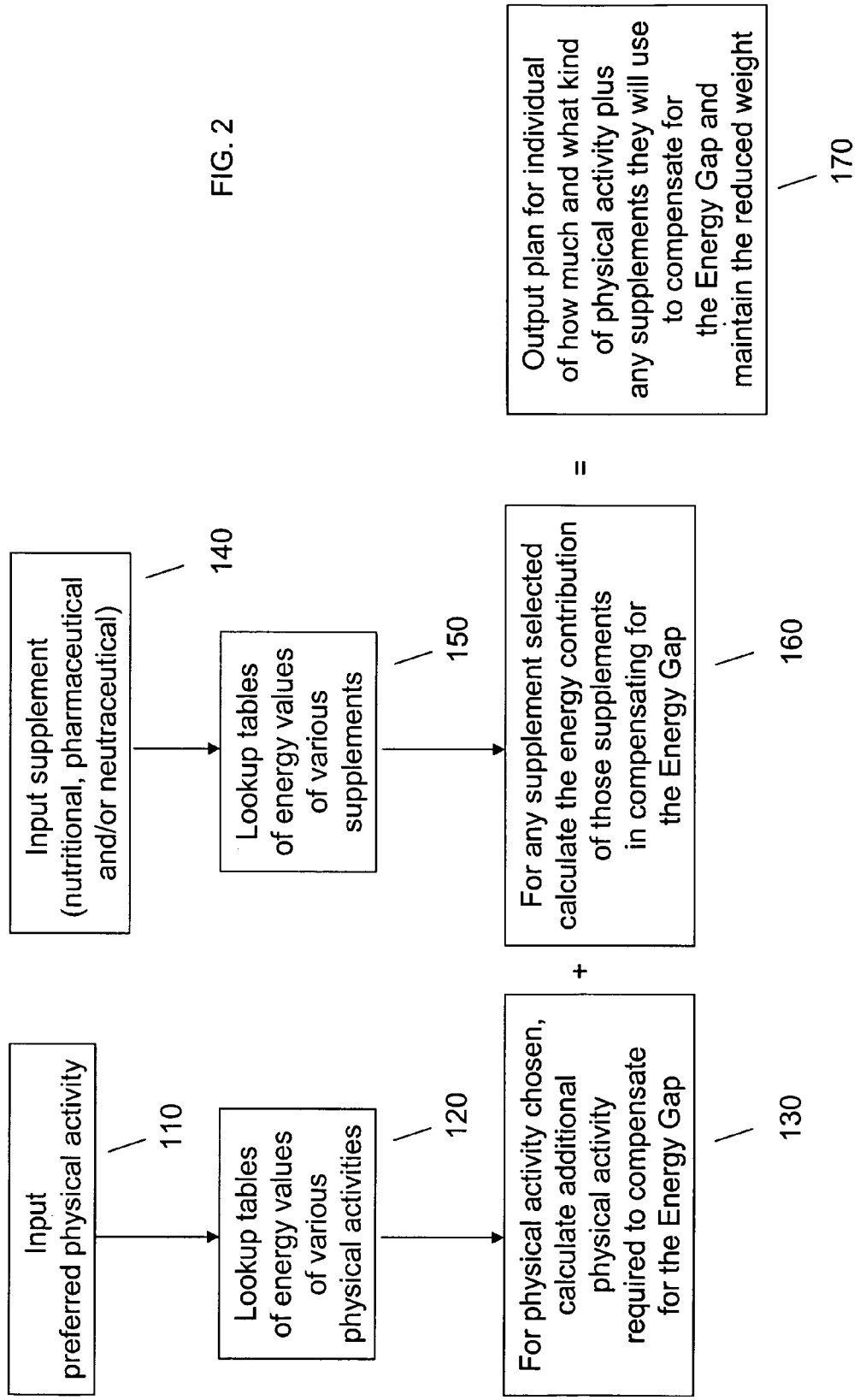
FIG. 2 illustrates a flow diagram in accordance with another aspect of the invention of FIG. 1.

Another aspect of the invention, illustrated in FIG. 2, provides a way to compensate for the Total Energy Gap™ 100 through one or more of physical activity, food, dietary supplements or pharmaceutical aids. It is also within the scope of the present invention to compensate for the Activity Energy Gap™ 60 and/or the RMR Energy Gap™ 30 instead of the Total Energy Gap™100. As illustrated in FIG. 2, the user selects a preferred physical activity 110 from a list. It is also possible that the activity is either written in or spoken by the user; however, in such a configuration it is possible that the activity would not be recognized by the system. In such case the system could be designed to default to an operator, could request additional information from the user such as similar or related activities, could provide a default activity or could provide a list of activities from which the user could select the closest one. Once the activity selection is received by the system, the system determines a value of energy 120 for the preferred physical activity chosen. This determination can be done through a lookup table or by accessing other programs on the Internet, etc. It is also possible that the user does not wish to perform any physical activity in which case the system could design a program based on no physical activity.

Similar to the use of physical activity to compensate for the Energy Gap™, the system may also employ information provided from the user relating to nutritional or pharmaceutical tools 140 that can be used. As with the physical activity 110, this information can be selected from a list, written in or spoken by the user. This supplement information 140 may be used to determine a value of energy 150 for the preferred supplement chosen. This determination can be done through a lookup table or by accessing other programs on the Internet, etc. It is also possible that the user does not wish to utilize any supplements (nutritional, pharmaceutical or neutraceuticals) 140 in which case the system could design a program based on no supplement use.

Once the system has determined the Total Energy Gap™, the physical activity energy value, and the supplement energy value it uses that information to configure a program for the user which will assist that user in maintaining the weight loss (actual or desired). The program may include a caloric amount, a physical activity amount and type and a supplement amount and type. The system may then provide the information to the user in the form of a graphical analysis, a verbal list or a text list. It is also possible that the user may be provided the option at this point to tweak the plan to make it more appealing. For instance, the user could be provided with the ability to increase or decrease one or more of the suggested program details and the program could automatically reconfigure all of the program details accordingly. Those skilled will recognize that this feature could also require the user to take some action which causes the system to reconfigure the program (i.e. it does not need to be automatic).

FIG. 3 illustrates a sample application of an embodiment of the present invention. The system prompts the user to enter current height 200, weight 220, gender 230 and age 240. In this case the user input is: Height (inches)=68; Current Weight (lbs)=205; Gender=Female; and Age=40. The system also requests the amount of weight loss 250, the amount of physical activity prior to the weight loss 260 and the status of the user's weight in the 3 months prior to the weight loss 270. In this example, the user entered a weight loss of 30 lbs, minimal physical activity and a gain of between 3 and 5 pounds just prior to the weight loss.

The system prompts the user to select pre-weight loss daily physical activity, in steps or minutes, by direct input or by choosing from a multiple choice list. For example the user chooses from physical activity levels such as:

(1) Minimal: less than 3,000 steps/day or 30 minutes of activity;

(2) Low/Moderate: 3,000-5,000 steps or 30-45 minutes of activity;

(3) Moderate: 5,000-7,000 steps or 45 minutes-1 hour of activity; or (4) High: 7,000+ steps or 1+ hour of activity. In the example of FIG. 3 the user selected "Minimal: less than 3,000 steps/day or 30 minutes of activity."

The program provides a baseline number of calories burned in the selected physical activity, based on a Steps/Calorie value table and determines calories burned in physical activity with current weight. The difference in the two determinations reflects how much less a constant physical activity is worth when body weight is reduced. Based on the above user input the application makes the following determinations: Estimated Baseline Steps=2000; Base Step Calories=138.9529; Current Step Calories=121.2142; and Activity Gap Calories=17.73866.

The program requests the weight stability information as follows: "In 3 months before you started to lose weight which option best describes your weight trend?" The present invention allows the user to enter direct input or choose from a multiple choice list. For example the user is able to select form choices such as:

(1) I gained more than 5 lbs in those 3 months;
(2) I gained between 3 and 5 lbs in those 3 months;
(3) I gained between 1 and 3 lbs in those 3 months; or
(4) I stayed about the same weight for those three months.

In the particular example in FIG. 3 the user chose "I gained between 3 and 5 lbs in those 3 months."

The application uses at least part of the information provided to determine a calorie gap, which for this case is 240 (each pound lost is worth 8 calories per day in reduced RMR). This information may be provided to the user but it is not required.

Figure 4:
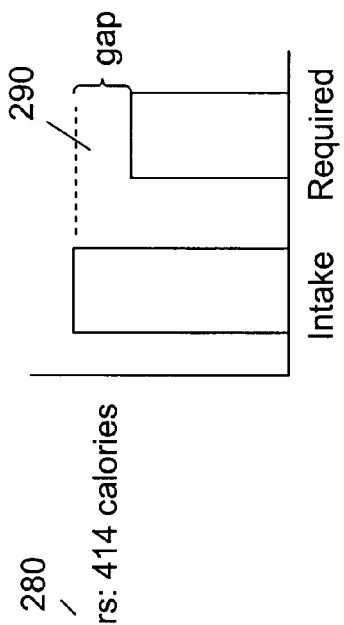
FIG. 4 illustrates sample maintenance program according to the present invention.

The system also prompts the user for their preferred physical activity as: "What is your preferred physical activity?" Again the user is able to select form a list of physical activities (e.g. walking or running). In the example of FIG. 4 the user chose running.

Based on user input the application then determines the weight gain adjustment which in this example is 156. The weight gain adjustment adds calories to the user's Energy Gap™ if they were gaining weight before they lost weight meaning they were not in energy balance before weight loss.

The example of FIG. 4 also generates the following information:

(1) Total Energy Gap™ (calories/day)=414;
(2) Total Gap Steps=6,831 which converts Total Energy Gap™ to steps;
(3) Total Gap Minutes=53 which converts Total Energy Gap™ to minutes of activity, based on the activity that the user chose.

In the aspect of the invention illustrated in FIG. 4, a program is created based on user preferences and available supplements. The system allows the user to input supplements that will be used to assist in the maintenance program. The system is flexible in that the user is able to adjust their answers to optimize a plan that is right for them. In this example a Slim-Fast® product is employed. The system prompts the user to input how Slim-Fast will be employed. A multiple choice list is provided as follows:

(1) Replace Lunch daily with Slim-Fast;
(2) Replace Dinner daily with Slim-Fast;
(3) Replace a daily snack with Slim-Fast; or
(4) Will not use Slim-Fast to assist my weight maintenance.

In the example of FIG. 4, the user chose "Replace lunch daily with Slim-Fast". Based on this information, the application generates the following:

(1) Slim-Fast gap calories=364, the application determines the daily caloric value of the product choices offered, and subtracts the value of the user's choice from their Total Energy Gap™ to produce a "remaining gap calories" compensated for by physical activity.
(2) Slim-Fast gap steps=6954, the application then converts the remaining gap calories to steps;
(3) Slim-Fast gap minutes=46.97, the application converts the remaining gap calories to minutes of the user's preferred physical activity;
(4) Maximum Slim-Fast gap calories=289, the application determines the maximum assistance the product(s) in question can provide, and determines a maximum daily caloric value and subtracts it from the Total Energy Gap™ for remaining gap calories as above.
(5) Maximum Slim-Fast gap steps=4,768, the application converts the remaining gap calories to steps.
(6) Maximum Slim-Fast gap minutes=37.3, the application converts the remaining gap calories to minutes of the user's preferred physical activity.

Some of the above information may not be provided to the user. This is merely a design choice. Any or all of the information could be provided depending on how much or how little information is selected to be provided to the user.

FIG. 5 illustrates an example of possible feedback provided by the system in terms of number of additional steps or number of additional minutes of physical activity needed each day to compensate for the Energy Gap™ (not totals for the day just the additions to what is already being done). It provides this information in written and graphical form. The application provides output to the user such as: "Your Plan to fill your Energy Gap: At your current weight and goals, your daily additional activity requirements without supplements is 4560 steps or 24 minutes of additional activity. With your current choice to Replace Lunch daily with Slim-Fast you only need 3610 additional daily steps or 19 additional minutes of jogging activity to maintain your weight loss. With maximum Slim-Fast assistance, you would only need 2185 additional daily steps or 12 minutes of jogging activity to maintain your weight loss."

In another embodiment of the invention, the system converts the user's height to centimeters, in this example user height in cm=172.72; converts the user's weight to kilograms, in this example user weight in KG=92.98644 and calculates the user's current RMR (daily calories burned at rest) using all the input provided by them, in this example user current RMR=1677. The program then adds gap calories to the calories burned through baseline activity, in this example Total Activity Calories=535.2142. Total Energy Expenditure (TEE)=RMR+Total Activity Calories, this is the total calories the user needs to burn in a day to stay in energy balance. In this example User TEE=2,212,214.

The program them converts Total Activity Calories to steps, where in this example User Gap & Activity Steps=8,831, and calculates Total Activity less product value to steps where in this example User Gap & Activity Steps with Slim-Fast=8,006. The application also calculates Total Activity less maximum product value to steps, where in this example Maximum Slim-Fast gap & activity steps=6,768.

The program provides the user with text and graphical feedback on their total physical activity—sometimes with supplement use—to remain in energy balance and thus not regain the weight they have lost.

Figure 6:
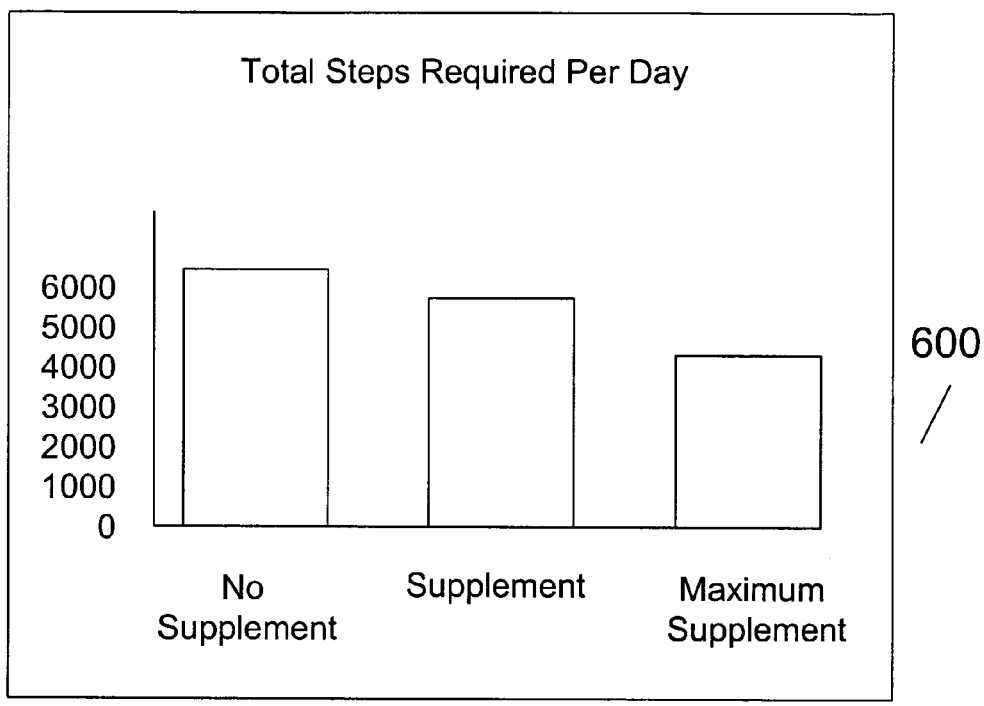
FIG. 6 illustrates a sample of a Total Weight Maintenance Plan with graphical and written representation.

FIG. 6 illustrates an example of a Total Weight Maintenance Plan in graphical and written form. As illustrated for this example, the system displays the following to the user: "Based on all the physical attributes you provided about yourself, your total unassisted physical activity requirements to maintain your weight loss is 6560 steps per day. With your current choice to Replace Lunch daily with Slim-Fast you only need 5610 total steps per day to maintain your weight loss. With maximum Slim-Fast assistance, you would only need 4185 total steps per day to maintain your weight loss."

Further, the program calculates the Total Energy Expenditure (TEE) and may provide feedback to the user, because research indicates that at least 25% of a person's TEE should come from physical activity. If it is less than 25%, it may cause the body to perform inefficiently, making it more difficult to achieve energy balance than the formulas would indicate. For this example the Activity as % of TEE=24%.

It will be understood that changes may be made in the above construction and in the foregoing sequences of operation without departing from the scope of the invention. For example, in the examples provided, most of the energy gap is filled with physical activity; however, while recommended this is not required. The energy gap could be filled with a reduction in caloric intake and/or with supplements. It is accordingly intended that all matter contained in the above description or shown in the accompanying drawings be interpreted as illustrative rather than in a limiting sense.

It is also to be understood that the following claims are intended to cover all of the generic and specific features of the invention as described herein, and all statements of the scope of the invention which, as a matter of language, might be said to fall therebetween.

Having described the invention, what is claimed as new and secured by Letters Patent is:

1. A method for determining an energy gap and creating a plan to compensate for the energy gap, the method comprising:

receiving at a processor a weight of a person, an amount of physical activity performed by a person for a period of time prior to a weight loss, a weight status for a period of time prior to said weight loss and an amount of weight loss;

said processor determining an energy value for the pre-weight loss physical activity based on a pre-weight loss weight, another energy value for the pre-weight loss physical activity based on the amount of weight loss, and an energy value for the amount of weight loss;

said processor determining a difference between the energy value for the pre-weight loss physical activity and the another energy value for the pre-weight loss physical activity based on the amount of weight loss;

said processor determining an adjustment value based on the weight status;

said processor summing the energy value for the weight loss, the difference between the energy values for the pre-weight loss physical activity, and the adjustment value to determine an energy requirement difference caused by the weight loss;

said processor determining a plan for compensating for the energy requirement difference; and, said processor providing the plan to a user interface.

2. The method according to claim 1 wherein determining a plan for compensating for the energy requirement difference comprises calculating an amount of physical activity, an amount of food and an amount of supplement required to compensate for the energy requirement difference caused by the weight loss.

3. The method according to claim 1 further comprising receiving at the processor at least one statistic selected from the group consisting of a gender and an age.

4. The method according to claim 1 further comprising providing the user the ability to make an adjustment to the plan.

5. The method according to claim 1 further comprising receiving a type of physical activity performed by the person.

6. The method according to claim 1 wherein at least one of said amount of physical activity performed by a person for a period of time prior to a weight loss, weight status and amount of weight loss is received in the form of a response to a multiple choice question.

7. The method according to claim 1 wherein said amount of weight loss is received in the form of a pre-weight loss weight and a post weight loss weight.

\* \* \* \* \*